(12) United States Patent
Krafczyk et al.

(10) Patent No.: US 6,274,753 B1
(45) Date of Patent: Aug. 14, 2001

(54) PROCESS FOR THE PREPARATION OF SULFUR- AND PHOSPHORUS-CONTAINING ORGANOSILICON COMPOUNDS

(75) Inventors: Roland Krafczyk, Langenselbold; Jörg Münzenberg; Gerd Rainhard Zezulka, both of Hanau, all of (DE)

(73) Assignee: Degussa AG, Düsseldorf (DE)

( * ) Notice: Subject to any disclaimer, the term of this patent is extended or adjusted under 35 U.S.C. 154(b) by 0 days.

(21) Appl. No.: 09/709,572

(22) Filed: Nov. 13, 2000

(30) Foreign Application Priority Data

Nov. 13, 1999 (DE) .............................. 199 54 815

(51) Int. Cl.⁷ ................ C07F 7/08; C07F 7/18
(52) U.S. Cl. ................................................ 556/405
(58) Field of Search ............................. 556/405

(56) References Cited

U.S. PATENT DOCUMENTS 4,152,347 * 5/1979 Pletka et al. ................ 556/405
4,416,830 * 11/1983 Morr et al. .............. 556/405 X

FOREIGN PATENT DOCUMENTS 26 58 368    7/1978 (DE) .

OTHER PUBLICATIONS

Murav'ev I.V.: "Reactions of diphosphorus pentasulfide with alkyl halides", Journal of General Chemistry USSR., Bd. 45, Nr. 8 –Jan. 20, 1976.

Nizamov I.S., etal., "Influence of nucleophilic reagents on the reactions of phosphorus sulfides and alkyl homologs of Davy's reagent with alkyl halides and dialkyl disulfides" Phosphorus, Sulfur Silicon Relat. Elem. 1998; vol. 132, pp. 85–100.

Russian Academy of Sciences; A.E. Arbuzov Institute of Organic and Physical Chemistry; Kazan; Russia, Dec. 18, 1997.

* cited by examiner

Primary Examiner—Paul F. Shaver
(74) Attorney, Agent, or Firm—Smith, Gambrell & Russell, LLP

(57) ABSTRACT

Process for the preparation of sulfur- and phosphorus-containing compounds of the formula:

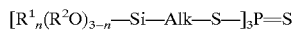

in which halogen-containing silanes of the formula $R^1_n(R^2O)_{3-n}$—Si—Alk—Hal are reacted with phosphorus pentasulfide ($P_4S_{10}$) and a metal sulfide.

6 Claims, No Drawings

PROCESS FOR THE PREPARATION OF SULFUR- AND PHOSPHORUS-CONTAINING ORGANOSILICON COMPOUNDS

INTRODUCTION AND BACKGROUND

The present invention relates to a process for the preparation of sulfur- and phosphorus-containing organosilicon compounds.

German application DE 2658368 C2 discloses compounds of the formula

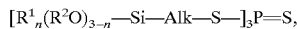

$[R^1_n(R^2O)_{3-n}-Si-Alk-S-]_3P=S$, in which Alk denotes an alkylene group having 2 to 4 carbon atoms, $R^1$, $R^2$ denote an alkyl group having 1 to 5 carbon atoms, a cycloalkyl group having 5 to 8 carbon atoms, a phenyl group, a benzyl group or the 2-methoxyethyl group, wherein $R^1$ or $R^2$ in each case can have identical or different meanings, and n=0, 1 or 2.

For the preparation of these compounds, thiophosphoryl chloride or bromide is reacted with a mercaptosilane of the formula

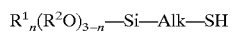

$R^1_n(R^2O)_{3-n}-Si-Alk-SH$ with the abovementioned meanings.

Mercaptosilanes are expensive starting compounds, since as a rule they are prepared from the corresponding chlorosilanes (EP 471 164 B1, DE-AS 20 35 619, DE-PS 33 46 910, U.S. Pat. No. 3,849,471, GB-PS 1 102 251).

The disadvantage of these known processes is that expensive mercaptosilane is used as an educt for the preparation of the abovementioned phosphorus-containing compounds.

An object of the present invention is to provide an alternative process for the preparation of sulfur- and phosphorus-containing organosilicon compounds.

SUMMARY OF THE INVENTION

The above and other objects of the invention can be achieved by a process for the preparation of sulfur- and phosphorus-containing compounds of the formula

$[R^1_n(R^2O)_{3-n}-Si-Alk-S-]_3P=S$, in which Alk denotes an alkylene group having 1 to 10 carbon atoms, $R^1$, $R^2$ denote an alkyl group having 1 to 5 carbon atoms, a cycloalkyl group having 5 to 8 carbon atoms, a phenyl group, a benzyl group or a 2-methoxyethyl group, wherein $R^1$ or $R^2$ in each case can have identical or different meanings, and n=0, 1 or 2, which is characterized in that halogen-containing silanes of the formula

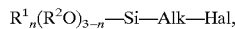

$R^1_n(R^2O)_{3-n}-Si-Alk-Hal$, in which Alk denotes an alkylene group having 1 to 10 carbon atoms, $R^1$, $R^2$ denote an alkyl group having 1 to 5 carbon atoms, a cycloalkyl group having 5 to 8 carbon atoms, a phenyl group, a benzyl group or a 2-methoxyethyl group, wherein $R^1$ or $R^2$ in each case can have identical or different meanings, Hal denotes a halogen, preferably chlorine or bromine, and n=0, 1 or 2, are reacted with phosphorus pentasulfide ($P_4S_{10}$) and a metal sulfide.

The reaction can take place according to the equation

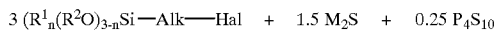

$3 (R^1_n(R^2O)_{3-n}Si-Alk-Hal) + 1.5 M_2S + 0.25 P_4S_{10}$

$\downarrow -3 MCl$

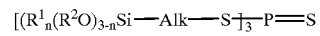

$[(R^1_n(R^2O)_{3-n}Si-Alk-S-]_3-P=S$

The reaction can be carried out in a solvent, preferably hexane, acetonitrile, toluene, heptane or cyclohexane. Since phosphorus pentasulfide dissolves in $R^1_n(R_2O)_{3-n}-Si-Alk-Hal$, the reaction can be carried out without a solvent. The reaction can be carried out with exclusion of air and moisture.

The reaction can be carried out under an inert gas, preferably nitrogen, argon or helium. The reaction can be carried out at temperatures of 20° to 300° C., preferably 150° to 250° C. Sodium sulfide ($Na_2S$), potassium sulfide ($K_2S$) or ammonium sulfide (($NH_4)_2S$) can be used as the metal sulfide.

The sulfur- and phosphorus-containing compounds prepared according to the invention can be used in rubber mixtures.

DETAILED EMBODIMENT OF THE INVENTION

Example

A mixture of 30.8 g (69.2 mmol) $P_4S_{10}$, 200.0 g (830.3 mmol) chloropropyltriethoxysilane and 32.4 g (415.3 mmol) sodium sulfide ($Na_2S$) is initially introduced into a 500 ml three-necked flask in an argon atmosphere and is heated to 200° C. After stirring at 200° C. for 2.5 h, insoluble constituents are filtered off. All the volatile constituents are removed in vacuo. 168.5 g (79% yield) of tetrathiophosphoric acid S,S,S-tris (triethoxysilylpropyl) ester are obtained as a pale yellow clear liquid.

$^1$H-NMR (CDCl$_3$): δ0.75 (m, $^2J_{H-Si}$=111.4 Hz, 6H, Si—C$\underline{H}_2$—CH$_2$—CH$_2$—S—), 1.22 (t, $^3J_{H-H}$=7.4 Hz, 27H, C$\underline{H}_3$—CH$_2$—O—Si), 1.85 (dm, $^3J_{H-H}$=7.5 Hz, 6H, Si—CH$_2$—C$\underline{H}_2$—CH$_2$—S—), 3.02 (dt, $^3J_{H-H}$= 7.5 Hz, $^3J_{H-P}$=17.0 Hz, 6H, Si—CH$_2$—CH$_2$—C$\underline{H}_2$—S—), 3.82 (q, $^3J_{H-H}$=7.4 Hz, 18H, CH$_3$—C$\underline{H}_2$—O—Si). $^{31}$P-NMR (CDCl$_3$): δ94.5 (s)

Further variations and modifications of the present invention will be apparent to those skilled in the art from a reading of the foregoing and are intended to be encompassed by the claims appended hereto.

German patent application 199 54 815.3 is relied on and incorporated herein by reference.

What is claimed is:

1. A process for the preparation of a sulfur- and phosphorus-containing compound of the formula

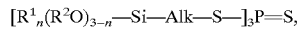

$[R^1_n(R^2O)_{3-n}-Si-Alk-S-]_3P=S$, in which Alk denotes an alkylene group having 1 to 10 carbon atoms, $R^1$, $R^2$ denote an alkyl group having 1 to 5 carbon atoms, a cycloalkyl group having 5 to 8 carbon atoms, a phenyl group, a benzyl group or a 2-methoxyethyl group, wherein $R^1$ or $R^2$ in each case can have identical or different meanings, and n=0, 1 or 2, comprising reacting a halogen-containing silane of the formula

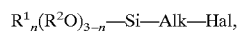

$R^1_n(R^2O)_{3-n}-Si-Alk-Hal$, in which Alk denotes an alkylene group having 1 to 10 carbon atoms, $R^1$, $R^2$ denote an alkyl group having 1 to 5 carbon atoms, a cycloalkyl group having 5 to 8 carbon atoms, a phenyl group, a benzyl group or a 2-methoxyethyl group, wherein $R^1$ or $R^2$ in each case can have identical or different meanings, Hal denotes a halogen and n=0, 1 or 2, with phosphorus pentasulfide ($P_4S_{10}$) and a metal sulfide.

2. The process for the preparation of a sulfur- and phosphorus-containing compound according to claim 1, wherein the metal sulfate is chlorine or bromine.

3. The process for the preparation of a sulfur- and phosphorus-containing compound according to claim 1, wherein the metal sulfide is sodium sulfide ($Na_2S$), potassium sulfide ($K_2S$) or ammonium sulfide ($(NH_4)_2S$).

4. The process for the preparation of a sulfur- and phosphorus-containing compound according to claim 1, further comprising carrying out the reaction in a solvent.

5. The process for the preparation of a sulfur- and phosphorus-containing compound according to claim 1, further comprising reacting in the absence of a solvent.

6. The process for the preparation of a sulfur- and phosphorus-containing compound according to claim 1, further comprising reacting at a temperature of 150° to 250° C.

* * * * *